United States Patent [19]

Grollier

[11] Patent Number: 4,840,787

[45] Date of Patent: Jun. 20, 1989

[54] DENTIFRICE CONTAINING A POLY(HYDROXYPROPYL ETHER) NON-IONIC SURFACTANT AND A SPECIFIED CATIONIC POLYMER

[75] Inventor: Jean F. Grollier, Paris, France

[73] Assignee: L'Oreal, Paris, France

[21] Appl. No.: 95,591

[22] Filed: Jul. 14, 1987

[30] Foreign Application Priority Data

Sep. 15, 1986 [LU] Luxembourg ............................ 86586

[51] Int. Cl.$^4$ .......................... A61K 7/16; A61K 7/18; A61K 7/22
[52] U.S. Cl. ....................................................... 424/52
[58] Field of Search ....................................... 424/49–58

[56] References Cited

U.S. PATENT DOCUMENTS

| | | | |
|---|---|---|---|
| 3,910,862 | 10/1975 | Barabas et al. | 260/79.3 |
| 4,031,307 | 6/1977 | DeMartino et al. | 536/114 |
| 4,157,387 | 6/1979 | Benedict | 424/54 |
| 4,307,079 | 12/1981 | Zorayan et al. | 424/70 |
| 4,391,798 | 7/1983 | Tavss et al. | 424/52 |
| 4,453,979 | 6/1984 | DeMasi et al. | 106/188 |

FOREIGN PATENT DOCUMENTS 2021949 12/1979 United Kingdom .
2140691 12/1984 United Kingdom .

OTHER PUBLICATIONS

Japan Abstract of Japan, vol. 9, No. 108, May 11, 1985.

*Primary Examiner*—Shep K. Rose
*Attorney, Agent, or Firm*—Fleit, Jacobson, Cohn, Price, Holman & Stern

[57] ABSTRACT

Dentifrice containing, in combination, (A) a poly(hydroxypropyl ether) nonionic surfactant, and (B) a cationic polymer selected from the group consisting of (i) a vinylpyrrolidone/dialkylaminoalkyl or -hydroxyalkyl acrylate or methacrylate, quaternized or nonquaternized and (ii) a cationic polysaccharide.

This dentifrice is characterized by good foamability, pleasant taste and it does not attack the buccal mucosae and the gums.

11 Claims, No Drawings

DENTIFRICE CONTAINING A POLY(HYDROXYPROPYL ETHER) NON-IONIC SURFACTANT AND A SPECIFIED CATIONIC POLYMER

The invention relates to a dentifrice with improved foaming properties, without bitterness and not attacking the mucosae and the gums, containing, in combination, a poly(hydroxypropyl ether) nonionic surfactant and a specified cationic polymer chosen from the group consisting of (i) the quaternized or non quaternized vinylpyrrolidone/di($C_{1-4}$) alkylamino($C_{2-18}$) alkyl acrylate or methacrylate or vinylpyrrolidone/di($C_{1-4}$) alkylamino-2-hydroxypropyl acrylate or methacrylate copolymers and (ii) cationic poly-saccharides.

The applicant has already described in Belgian Pat. No. 899,780 a cleaning product for tooth and mouth care and in particular a dentifrice which has a pleasant taste, which is not bitter and which does not attack the mucosae, this dentifrice containing a poly(hydroxypropylether) nonionic surfactant. This dentifrice has fairly good foamability.

However, although the foamability of dentifrice compositions is not related to the cleaning power, confusion appears to exist in the users' minds and, for the majority of them, the idea that a dentifrice cleans sufficiently only if it foams well is quite widely held and foaming dentifrices are in the greatest demand by the users.

It has therefore been found desirable to investigate a dentifrice containing a poly(hydroxypropyl ether) with improved foamability, without a bitter taste and not attacking the buccal mucosa and the gums.

French Pat. No. 2,271,840 discloses a composition containing abrasive agents coated with a water-soluble cationic polymer, this coating being intended to prevent or to reduce the absorption of cationic germicidal agents by the abrasive. This patent also discloses the use of such an abrasive composition in dentifrices.

Research carried out by the applicant has shown that the combination of a poly(hydroxypropyl ether) nonionic surfactant with certain cationic polymers did not make it possible to produce dentifrice compositions with improved foamability and, in some cases, had the disadvantage of leaving a rough deposit on the teeth and the gums.

It has been found that the combination of a poly-(hydroxylpropyl ether) surface-active agent with a cationic polymer as referred to hereinafter, makes it possible to improve the foamability while leaving the teeth smooth and gleaming.

The subject of the invention is a dentifrice containing, in combination, a poly(hydroxypropyl ether) non-ionic surfactant with a water-soluble cationic polymer, chosen from the group consisting of:

(i) a vinylpyrrolidone/di($C_1$–$C_4$) alkylamino ($C_2$–$C_{18}$)-alkyl acrylate or methacrylate or vinylpyrrolidone/di($C_{1-4}$)-alkylamino-2-hydroxypropyl acrylate or methacrylate copolymer, quaternized or otherwise, and, if desired, a copolymer of another vinyl monomer which is copolymerizable with vinyl-pyrrolidone.

The quaternary copolymers consist of 20 to 99 moles % of vinylpyrrolidone, 1 to 80 moles % of di($C_1$–$C_4$)alkyl-amino($C_2$–$C_{18}$) alkyl acrylate or methacrylate or di($C_1$–$C_4$)-alkylamino-2-hydroxypropyl acrylate or methacrylate, quaternized, and 0 to 50 moles % of a vinyl monomer which is copolymerizable with N-vinylpyrrolidone.

This vinyl monomer is preferably an alkyl vinyl ether, an acrylate or methacrylate, styrene, vinyl acetate, acrylamide or methacrylamide and their N-substituted derivatives, and esters of crotonic acid.

These compounds are described in further detail in French Pat. No. 2,077,143 and in U.S. Pat. No. 3,910,862 the subject-matter of which is incorporated in the present application by way of reference.

The nonquaternized copolymers consist of 99.5 to 45 moles % of vinylpyrrolidone, 0.5 to 50 moles % of di($C_1$–$C_4$)alkylamino($C_2$–$C_{18}$)alkyl acrylate or methacrylate and 0 to 50 moles % of a vinyl monomer which is copolymerizable with vinylpyrrolidone. This vinyl monomer is preferably chosen from those mentioned above. These copolymers are described in French Pat. No. 2,393,573 the subject-matter of which is incorporated in the present application by way of reference;

(ii) a cationic polysaccharide and in particular a quaternary polygalactomannane ether obtained by the reaction of guar gum or of carob gum with a quaternary ammonium compound of formula:

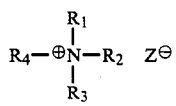

where $R_1$, $R_2$ and $R_3$, which are identical or different, denote an alkyl, substituted alkyl, alkenyl or aryl radical, the alkyl and alkenyl radicals preferably containing from 1 to 4 carbon atoms;

Z is an anion;

$R_4$ denotes a group:

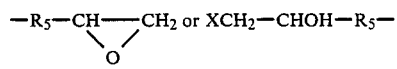

where $R_5$ is a divalent alkylene radical containing from 1 to 3 carbon atoms and X denotes a halogen atom and preferably chlorine or bromine.

Among the copolymers (i), preference is given to a quaternized copolymer of vinylpyrrolidone and dimethylaminoethyl methacrylate, especially the copolymer with a molecular weight of the order of 1,000,000 sold under the name Gafquat 755 and the copolymer with a molecular weight of the order of 100,000, sold under the name Gafquat 734 by the GAF company. More particular preference is given to Gafquat 755.

Among the nonquaternized copolymers, preference is given to the vinylpyrrolidone/dimethylaminoethyl methacrylate copolymers sold by the GAF company under the names "copolymers 845, 937 and 958" and having the following characteristics:

"Copolymer 845": a viscosity of 20 to 40 pascal seconds (Pa.s) (200 to 400 poises) measured in a Brook-field viscometer at 20 rpm with a no. 7 needle, at a concentration of 20% by weight in water at a temperature of 25° C.; an average molecular weight of the order of 1,000,000.

"Copolymer 937": a viscosity of 30 to 70 Pa.s (300 to 700 poises) measured in a Brookfield viscometer under the same conditions as above, and an average molecular weight of the order of 1,000,000.

"Copolymer 958": an average molecular weight of the order of 100,000.

Among the polymers (ii), preference is given to the hydroxypropylated and quaternized quar gum produced by the reaction of 2,3-epoxypropyltrimethylammonium chloride with guar gum and marketed by the Meyhall company under the name Jaguar C 13 S.

The cationic polymer content in the dentifrice is 0.1 to 0.4% preferably 0.2 to 0.3% by weight based on the total weight of the dentifrice.

The poly(hydroxypropyl ether) nonionic surfactants to be employed in the dentifrice according to the invention are chosen from the compounds of formulae (I) and (II) below and/or from the compounds prepared according to the process described in paragraphs (3) and (4) below:

(1) 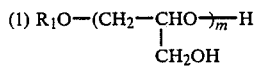 (I)

where $R_1$ denotes a radical or a mixture of alkyl radicals containing from 10 to 14 carbon atoms and m is an integer or decimal from 2 to 10 and preferably from 3 to 6. These compounds of formula (I) may be prepared according to the process described in French Pat. No. 1,477,048 or in U.S. Pat. No. 3,578,719;

(2) 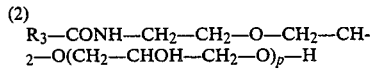 (II)

where $R_3$ denotes a radical or a mixture of alkyl and/or alkenyl radicals containing from 11 to 17 carbon atoms and p denotes an integer or decimal from 1 to 5 and preferably 1.5 to 4. These compounds of formula (II) may be prepared according to the process described in French Pat. No. 2,328,763 or according to U.S. Pat. No. 4,307,079; (3) compounds prepared by alkali-catalysed condensation of 2 to 10 moles and preferably 2.5 to 6 moles of glycidol with an alpha-diol or a mixture of $C_{10}$–$C_{14}$ alpha-diols, at a temperature of 120°–180° C. and preferably 140° to 160° C., the glycidol being added slowly, according to the process described in French Pat. No. 2,091,516 or in U.S. Pat. No. 3,821,372; (4) compounds prepared by acid-catalysed condensation of 2 to 10 and preferably 2.5 to 6 moles of glycidol per mole of alcohol or of alpha-diol containing 10 to 14 carbon atoms at a temperature of 50° to 120° C., the glycidol being added slowly to the alcohol or to the alpha-diol, the process for the preparation of these compounds being described in French Pat. No. 2,169,787 or U.S. Pat. No. 4,515,775.

The subject-matter of the patents referred to in paragraphs (1) to (4) above is incorporated in the description of the present application by way of reference.

Among the poly(hydroxypropyl ether) nonionic surfactants described in paragraphs (1), (2), (3) and (4) above, preference is given to the following compounds:

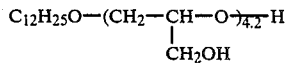 (III)

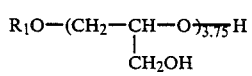 (IV)

where $R_1$ denotes a mixture of $C_{10}H_{21}$ and $C_{12}H_{25}$ alkyl radicals;

compounds prepared by alkali-catalysed condensation of 3.5 moles of glycidol with a mixture of alpha-diols containing from 11 to 14 carbon atoms, according to the process described in French Pat. No. 2,091,516 or in U.S. Pat. No. 3,821,372;

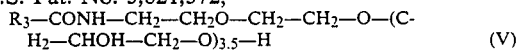 (V)

where $R_3$ denotes a mixture of radicals comprising the following alkyl and alkenyl radicals: $C_{11}H_{23}$, $C_{13}H_{27}$, radicals derived from copra fatty acids, radical derived from oleic acid.

The compounds prepared by condensation of 3.5 moles of glycidol with a mixture of $C_{11}$–$C_{14}$ alpha-diols according to French Pat. No. 2,091,516 or U.S. Pat. No. 3,821,372 are particularly preferred.

In the dentifrice compositions according to the invention:

the poly(hydroxypropyl ether) surfactant is present in proportions of 0.1 to 4% and preferably 0.2 to 2% by weight based on the total weight of the composition.

The dentifrice according to the invention generally contains one or more abrasive polishing agents which are predominantly insoluble in water.

Among these polishing agents there may be mentioned, by way of example, sodium or potassium metaphosphates, tricalcium phosphate, calcium phosphate dihydrate, dicalcium phosphate, calcium pyrophosphate, calcium carbonate, alumina, alumina hydrates and in particular trihydrates, silica, aluminium or zirconium silicates, bentonite, as well as magnesium orthophosphate or trimagnesium phosphate.

In the case of transparent gels, a polishing agent based on colloidal silica or complex alkali metal alumino-silicates will preferably be employed.

The abrasive polishing agent represents 10 to 80% and preferably 15 to 65% of the total weight of the dentifrice.

The dentifrice according to the invention may also contain one or more bactericidal agents intended to combat the formation of dental plaque. These bactericidal agents are generally cationic nitrogen compounds. Among these cationic compounds the following may be mentioned by way of example:

diisobutylphenoxyethoxyethyldimethylbenzylammonium chloride,
dodecyltrimethylammonium bromide,
dodecyldimethyl(2-phenoxyethyl)ammonium bromide,
benzyldimethylstearylammonium chloride,
cetylpyridinium chloride,
quaternized 5-amino-1, 3-bis(2-ethylhexyl)-5-methyl-hexahydroxypyrimidine,
trimethylcetylammonium bromide,
alkyldimethylhydroxyethylammonium bromide (where alkyl denotes a mixture of radicals derived from copra fatty acids),
chlorhexidine,
alexidine, and
cationic tertiary aliphatic amines.

These bactericidal agents are generally present at between 0.005 and 10% and preferably between 0.05 and 2% by weight based on the total weight of the composition.

The dentifrice according to the invention also contains water or a humectant in a proportion of 10 to 80% of the total weight of the composition. This humectant is advantageously chosen from the group consisting of glycerine, sorbitol, propylene glycol, polyethylene glycols of low molecular weight such as polyethylene glycols 400 and 2000.

The dentifrice may also contain cohesion agents. These are generally natural resins or synthetic thickeners.

Gum tragacanth, xanthan gums and guar, carob or carragheen gums may be mentioned as natural resins.

The synthetic thickeners employed are essentially cellulose derivatives such as the sodium salt of carboxymethyl cellulose, methyl cellulose or hydroxyalkyl celluloses.

These cohesion agents may be present in the dentifrice according to the invention in a proportion varying between 0.1 and 10% and preferably between 0.2 and 3% by weight based on the total weight of the dentifrice.

The dentifrice according to the invention generally contains a sweetening agent in a concentration which generally varies between 0.1 and 2% based on the total weight of the dentifrice. Among the sweetening agents there may be mentioned by way of example: sucrose, lactose, fructose, xylitol, sodium cyclamate, maltose and sodium saccharinate.

The dentifrice according to the invention may contain a preservative in a quantity which is generally between 0.01 and 0.5% based on the total weight of the dentifrice. Among the preservatives there may be mentioned by way of example compounds such as formaldehyde and its derivatives, methyl para-hydroxybenzoate, propyl para-hydroxybenzoate and the like.

The dentifrice according to the invention may contain a flavouring substance in a proportion of between 0.5 and 5% by weight based on the total weight of the dentifrice. Among the flavouring substances the following may be mentioned by way of example: essences of mint (spear or pepper), aniseed, eucalyptus, cinnamon, clove, sage, liquorice, and essences of fruits such as lemon, orange, mandarine and strawberry or, if desired, methyl salicylate.

The pH of the dentifrice according to the invention is usually between 4.5 and 9 and preferably between 5.5 and 8.5. It is measured conventionally for a 20% dispersion of dentifrice in water.

Acidifying agents must generally be added. Citric acid, benzoic acid, monosodium phosphate and disodium phosphate may be mentioned by way of example among these.

Alkaline pH values are generally employed only in the case of dentifrices containing a compound which is unstable in a neutral or acidic medium as a polishing agent. This is the case, for example, with dentifrices containing calcium carbonate as a polishing agent.

The dentifrice according to the invention advantageously contains an anticaries agent. These are carriers of fluoride ions. Among these, the following inorganic fluorides may be mentioned by way of example: sodium, potassium, calcium, ammonium, zinc, tin, copper and barium fluorides, sodium or ammonium fluorosilicates, sodium or aluminium monofluorophosphate, aluminium difluorophosphate and sodium fluorozirconate. The most widely employed fluorine compounds are sodium fluoride, sodium monofluorophosphate and mixtures thereof.

The fluorine ion carrier is employed in a concentration such that the fluroide ion content does not exceed 1,500 ppm. By way of example, the concentrations employed are, in the case of sodium fluoride, between 0.05 and 0.25% and, in the case of sodium monofluorophosphate, these concentrations vary from 0.2 to 0.8% by weight of the total weight of the dentifrice.

The dentifrice according to the invention may also contain other adjuvants which are usually employed in compositions for tooth, gum and mouth care.

The examples which follow illustrate the invention without, however, limiting it.

EXAMPLE 1

A dentifrice of the following composition is prepared:

Alumina SH 100 sold by the Rhone-Poulenc company: 54.00 g
Xanthan gum sold by the Kelco company under the name Keltrol S: 1.45 g
Sorbitol as 70% strength aqueous solution: 30.00 g
Nonionic surfactant prepared by alkali-catalysed condensation of 3.5 moles of glycidol with a mixture of alpha-diols containing from 11 to 14 carbon atoms, according to the process described in French Pat. No. 2,091,516 or in U.S. Pat. No. 3,821,372: 1.00 g AS
Quaternized vinylpyrrolidone/dimethylaminoethyl methacrylate copolymer marketed at 20% AS by the General Aniline company under the name Gafquat 755: 0.25 g AS
(AS=active substance)
Sodium saccharinate: 0.15 g
Anhydrous monosodium phosphate: 0.60 g
Titanium dioxide: 0.60 g
Flavour, q.s. (sufficient quantity)
Preservative, q.s.
Water, q.s.: 100.00 g
Natural pH: 6.8

EXAMPLE 2

A dentifrice of the following composition is prepared:

Alumina SH 100 sold by the Rhone-Poulenc company: 54.00 g
Xanthan gum sold by the Kelso company under the name Keltrol S: 1.20 g
Sorbitol as 70% strength aqueous solution: 30.00 g
Nonionic surfactant prepared by alkali-catalysed condensation of 3.5 moles of glycidol with a mixture of alpha-diols containing from 11 to 14 carbon atoms according to the process described in French Pat. No. 2,091,516 or in U.S. Pat. No. 3,821,372: 1.00 g AS
Hydroxypropylated and quaternized quar gum sold by the Meyhall company under the name Jaguar C 13 S: 0.25 g AS
Sodium saccharinate: 0.15 g
Anhydrous monosodium phosphate: 0.60 g
Titanium dioxide: 0.60 g
Flavour, q.s.
Preservative, q.s.
Water, q.s.: 100.00 g
Natural pH: 6.7

The dentifrices prepared according to Examples 1 and 2 are markedly more foaming than a dentifrice of the same composition without the cationic polymer.

They leave no bitterness in the mouth and are readily removed, leaving the teeth smooth and gleaming.

EXAMPLE 3

A toothpaste of the following composition is prepared:

Nonionic surfactant of formula:

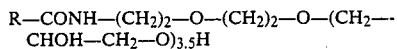

where R denotes the following mixture of alkyl and alkenyl radicals (% by weight) 35% $C_{12}H_{25}$—15% $C_{14}H_{29}$—15% oleyl radicals - 35% radicals derived from copra fatty acids: 1.20 g AS Quaternized polyvinylpyrrolidone copolymer having a molecular weight of approximately 100,000, sold at 50% AS by the GAF company under the name Gafquat 734: 0.20 g AS
Anhydrous dicalcium phosphate: 48.00 g
Sorbitol as 70% strength aqueous solution 27.00 g
Xanthan gum sold by the Kelco company under the name Keltrol S: 1.35 g
Sodium saccharinate: 0.25 g
Anhydrous disodium phosphate: 0.35 g
Anhydrous trisodium phosphate: 0.30 g
Titanium oxide: 0.50 g
Flavour, preservative, q.s.
Natural pH: 7.25
Water, q.s.: 100.00 g

EXAMPLE 4

A toothpaste of the following composition is prepared:
Nonionic surfactant of formula:

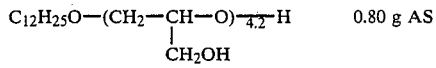

0.80 g AS

Poly(vinylpyrrolidone/diethylaminoethyl methacrylate) copolymer having an average molecular weight of approximately 1,000,000 and a viscosity of 20 to 40 pascal seconds (Pa.s) (200 to 400 poises), measured in a Brookfield viscometer at 20 rpm with a no.7 needle, at a concentration of 20% by weight in water, at a temperature of 25° C., sold by GAF company under the name Copolymer 845 at a concentration of 19% AS: 0.30 g AS Alumina SH 100: 50.00 g
Xanthan gum sold by the Kelco company under the name Keltrol S: 1.30 g
Sorbitol as 70% strength aqueous solution 25.00 g
Glycerine: 3.00 g
Sodium saccharinate: 0.15 g
Anhydrous monosodium phosphate: 0.60 g
Titanium oxide: 0.60 g
Flavour, preservative, q.s.
Natural pH: 6.25
Water, q.s.: 100.00 g

EXAMPLE 5

A toothpaste of the following composition is prepared:
Nonionic surfactant of formula:

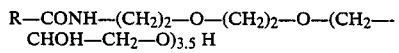

where R denotes the following mixture of alkyl and alkenyl radicals (% in weight) 35% $C_{12}H_{25}$—15% $C_{14}H_{29}$—15% oleyl radicals - 35% radicals derived from copra fatty acids: 1.10 g AS
Poly(vinylpyrrolidone/diethylaminoethyl methacrylate) copolymer having a viscosity of 30 to 70 pascal seconds (Pa.s) (300 to 700 poises), measured in a Brookfield viscometer at 20 rpm, with a no. 7 needle, at a concentration of 20% by weight in water, at 25° C., and whose average molecular weight is approximately 1 million, sold at 20% AS by the GAF company under the name Copolymer 937: 0.20 g AS Alumina SH 100: 52.00 g
Carragheenin/alginate complex sold by the Ceca-Satia company under the name Satiagum VZ 40: 1.35 g
Propylene glycol: 10.00 g
Sorbitol as 70% strength aqueous solution 15.00 g
Sodium saccharinate: 0.10 g
Anhydrous monosodium phosphate: 0.40 g
Titanium oxide: 0.60 g
Flavour, preservative, q.s.
Natural pH: 7.05
Water, q.s.: 100.00 g

I claim:

1. Dentifrice comprising:
(A) a poly(hydroxypropyl ether) nonionic surfactant, and
(B) a cationic polymer chosen from the group consisting of:
(i) a vinylpyrrolidone/di($C_{1-4}$)alkylamino($C_{2-18}$)-alkyl acrylate or methacrylate copolymer or a vinyl-pyrrolidone/di($C_1$-$C_4$)alkylamino-2-hydroxypropyl acrylate or methacrylate copolymer, quaternized or nonquaternized, and
(ii) a cationic polysaccharide which is hydroxypropylated and quaternized quar gum resulting from the reaction of 2,3-epoxypropyltrimethylammonium chloride with guar gum;
wherein the poly(hydroxypropyl ether) surfactant is present in an amount of 0.1 to 4% by weight based on the total weight of the dentifrice; and
wherein the cationic polymer is present in an amount of 0.1 to 0.4% by weight based on the total weight of the dentifrice.

2. Dentifrice according to claim 1, wherein the polymer (B) is a quaternized vinylpyrrolidone/dimethylaminoethyl methacrylate copolymer having a molecular weight of approximately 100,000 or approximately 1,000,000.

3. Dentifrice according to claim 1, wherein the polymer (B) is chosen from the following three vinylpyrrolidone/dimethylaminoethyl methacrylate copolymers:
(a) a vinylpyrrolidone/dimethylaminoethyl methacrylate copolymer having a viscosity of 20 to 40 pascal seconds (Pa.s) (200 to 400 poises), measured in a Brookfield viscometer at 20 rpm with a no. 7 needle, at a concentration of 20% by weight in water at a temperature of 25° C.; and having an average molecular weight of approximately 1,000,000;
(b) a vinylpyrrolidone/dimethylaminoethyl methacrylate copolymer having a viscosity of 30 to 70 Pa.s (300 to 700 poises), measured in a Brookfield viscometer under the same conditions as above, and having an average molecular weight of approximately 1,000,000; and
(c) a vinylpyrrolidone/dimethylaminoethyl methacrylate copolymer having an average molecular weight of approximately 100,000.

4. Dentifrice according to claim 1 wherein the poly(hydroxypropyl ether) nonionic surface agent is chosen from the group consisting of:
(1) the compounds of formula (I):

$$R_1O-(CH_2-CHO)_m-H \quad (I)$$
$$\phantom{R_1O-(CH_2-}|$$
$$\phantom{R_1O-(CH_2-}CH_2OH$$

where $R_1$ denotes a radical or a mixture of alkyl radicals containing from 10 to 14 carbon atoms and m is an integer or decimal from 2 to 10;
(2) the compounds of formula (II):

$$R_3-CONH-CH_2-CH_2-O-CH_2-CH_2-O(CH_2-CHOH-CH_2-O)_p H \quad (II)$$

where $R_3$ denotes a radical or a mixture of alkyl and/or alkenyl radicals containing from 11 to 17 carbon atoms and p denotes an integer or decimal from 1 to 5;
(3) the compounds prepared by alkali-catalysed condensation of 2 to 10 moles of glycidol with an alphadiol or a mixture of $C_{10}$-$C_{14}$ alpha-diols;
(4) the compounds prepared by acid-catalysed condensation of 2 to 10 moles of glycidol per mole of alcohol or of alpha-diol containing 10 to 14 carbon atoms.

5. Dentifrice according to claim 4, characterized in that the poly(hydroxypropyl ether) surfactant is selected from the group consisting of the compounds of formulae:

$$C_{12}H_{25}O-(CH_2-CH-O)_{\overline{4.2}}H \quad (III)$$
$$\phantom{C_{12}H_{25}O-(CH_2-}|$$
$$\phantom{C_{12}H_{25}O-(CH_2-}CH_2OH$$

$$R_1O-(CH_2-CH-O)_{\overline{3.75}}H \quad (IV)$$
$$\phantom{R_1O-(CH_2-}|$$
$$\phantom{R_1O-(CH_2-}CH_2OH$$

where $R_1$ denotes a mixture of $C_{10}$ and $C_{12}$ alkyl radicals.

6. Dentifrice according to claim 4, wherein the poly(hydroxypropyl ether) surfactant is the compound:

$$R_3-CONH-CH_2-CH_2-O-CH_2-CH_2-O-(CH_2-CHOH-CH_2-O)_{3.5} H \quad (V)$$

where $R_3$ denotes a mixture of radicals comprising the following alkyl and alkenyl radicals:
$C_{11}H_{23}$, $C_{13}H_{27}$, radicals derived from copra fatty acids, radical derived from oleic acid.

7. Dentifrice according to claim 4, wherein the poly(hydroxypropyl ether) surfactant is prepared by alkali-catalysed condensation of 3.5 moles of glycidol with a mixture of alpha-diols containing from 11 to 14 carbon atoms.

8. Dentifrice according to claim 1, containing from 10 to 80% by weight of a polishing agent.

9. Dentifrice according to claim 1, containing from 0.005 to 10% by weight of an antiplaque bactericidal agent.

10. Dentifrice according to claim 1, also containing a carrier of fluorine ions corresponding to a fluoride ion content not exceeding 1,500 ppm.

11. Dentifrice according to claim 1, also containing ingredients selected from the group consisting of humectants, cohesion agents, sweetening agents, preservatives and flavouring substances.

* * * * *